US00PP22282P2

(12) United States Plant Patent
Konst

(10) Patent No.: US PP22,282 P2
(45) Date of Patent: Nov. 29, 2011

(54) ***ALSTROEMERIA* PLANT NAMED 'KONCAYUKO'**

(50) Latin Name: *Alstroemeria hybrida*
Varietal Denomination: Koncayuko

(75) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 0 days.

(21) Appl. No.: 12/804,635

(22) Filed: Jul. 26, 2010

(51) Int. Cl.
*A01H 5/00* (2006.01)

(52) U.S. Cl. ..... Plt./309

(58) Field of Classification Search ..... Plt./309
See application file for complete search history.

(56) References Cited

U.S. PATENT DOCUMENTS

| | | | | |
|---|---|---|---|---|
| PP17,499 | P2 * | 3/2007 | Goemans | Plt./309 |
| PP20,976 | P2 * | 5/2010 | Konst | Plt./309 |
| PP22,010 | P2 * | 7/2011 | Herrera Valenzuela et al. | Plt./309 |

OTHER PUBLICATIONS

UPOV ROM GTITM Computer Database, GTI Jouve Retrieval Software 2011/01 "AU" Citation for 'Koncayuko'.*
UPOV ROM GTITM Computer Database, GTI Jouve Retrieval Software 2011/01 "QZ" Citation for 'Koncayuko'.*

* cited by examiner

*Primary Examiner* — Wendy C Haas
(74) *Attorney, Agent, or Firm* — C. A. Whealy

(57) ABSTRACT

A new and distinct cultivar of *Alstroemeria* plant named 'Koncayuko', characterized by its compact and mounding plant habit; sturdy and strong plants; vigorous growth habit; red purple-colored flowers; and good garden performance.

2 Drawing Sheets

Botanical designation: *Alstroemeria hybrida.*
Cultivar denomination: 'KONCAYUKO'.

BACKGROUND OF THE INVENTION

The present invention relates to a new and distinct cultivar of *Alstroemeria* plant, botanically known as *Alstroemeria hybrida,* typically grown as a potted garden *Alstroemeria,* and hereinafter referred to by the name 'Koncayuko'.

The new *Alstroemeria* plant is a product of a planned breeding program conducted by the Inventor in Nieuwveen, The Netherlands. The objective of the breeding program is to create new compact potted garden *Alstroemeria* plants that are early and freely flowering and have attractive leaf and flower coloration.

The new *Alstroemeria* plant originated from a self-pollination made by the Inventor in Nieuwveen, The Netherlands on Jun. 23, 2003 of a proprietary *Alstroemeria hybrida* selection identified as code number 03-24733-23, not patented. The new *Alstroemeria* plant was discovered and selected by the Inventor as a single flowering plant from within the progeny of the stated self-pollination in a controlled greenhouse environment in Nieuwveen, The Netherlands on Aug. 24, 2004.

Asexual reproduction of the new *Alstroemeria* plant by root divisions in a controlled greenhouse environment in Nieuwveen, The Netherlands since Oct. 18, 2006, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Koncayuko'. These characteristics in combination distinguish 'Koncayuko' as a new and distinct cultivar of *Alstroemeria* plant:

1. Compact and mounding plant habit.
2. Sturdy and strong plants.
3. Vigorous growth habit.
4. Red purple-colored flowers.
5. Good garden performance.

Plants of the new *Alstroemeria* can be compared to plants of the parent selection. Plants of the new *Alstroemeria* differ from plants of the parent selection in the following characteristics:

1. Plants of the new *Alstroemeria* are more compact than plants of the parent selection.
2. Plants of the new *Alstroemeria* and the parent selection differ in flower color as plants of the parent selection have purple-colored flowers.

Plants of the new *Alstroemeria* can be compared to plants of the *Alstroemeria hybrida* 'Konpride', disclosed in U.S. Plant Pat. No. 20,050. In side-by-side comparisons conducted in Nieuwveen, The Netherlands, plants of the new *Alstroemeria* differed from plants of 'Konpride' in the following characteristics:

1. Plants of the new *Alstroemeria* were broader than plants of 'Konpride'.
2. Plants of the new *Alstroemeria* had longer lower leaves than plants of 'Konpride'.
3. Flowers of plants of the new *Alstroemeria* were longer than flowers of plants of 'Konpride'.
4. Flowers of plants of the new *Alstroemeria* had longer perianth segments than flowers of plants of 'Konpride'.

5. Plants of the new *Alstroemeria* and 'Konpride' differed in flower color as plants of 'Konpride' had bright pink-colored flowers.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of typical flowering plants of 'Koncayuko' grown in containers.

The photograph on the second sheet is a close-up view of typical flowers of 'Koncayuko'.

DETAILED BOTANICAL DESCRIPTION

The aforementioned photographs and following observations and measurements describe plants of the new *Alstroemeria* grown during the summer in 19-cm containers in Nieuwveen, The Netherlands and under conditions and practices typical of commercial potted *Alstroemeria* production. For the first 16 weeks after planting, plants were grown in a glass-covered greenhouse and during the last 20 weeks of production plants were grown in an outdoor nursery. During the production of the plants, day temperatures ranged from 6° C. to 30° C. and night temperatures ranged from 6° C. to 16° C. Plants were 36 weeks old when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Koncayuko'.

Parentage:

*Female, or seed, parent.*—Proprietary *Alstroemeria hybrida* selection identified as code number 03-24733-23, not patented.

*Male or pollen parent.*—Proprietary *Alstroemeria hybrida* selection identified as code number 03-24733-23, not patented.

Propagation:

*Type.*—By root divisions.

*Root description.*—Thick, fleshy; color, close to 161C.

*Rooting habit.*—Freely branching; dense.

*Rhizome description.*—Shape: Elongate; rounded. Length: About 3.2 cm. Diameter: About 1 cm. Texture: Smooth. Color: Close to 163B.

Plant description:

*Plant habit.*—Compact and mounded; freely branching, bushy appearance; sturdy and strong plants; vigorous growth habit.

*Plant height.*—About 33 cm.

*Plant diameter* (*area of spread*).—About 50 cm.

Stem description:

*Aspect.*—Upright to somewhat outwardly spreading.

*Internode length.*—About 1.1 cm to 2.4 cm.

*Strength.*—Strong, sturdy.

*Texture.*—Smooth, glabrous.

*Color.*—Close to 144A; towards the base, close to 145A.

Foliage description:

*Arrangement.*—Alternate; below the peduncles in a single whorl; all leaves sessile.

*Length.*—About 5.1 cm to 5.8 cm.

*Width.*—About 1.2 cm to 1.4 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to N134A. Developing leaves, lower surface: Close to 138A. Fully expanded leaves, upper surface: Close to 137A; venation, close to N144A. Fully expanded leaves, lower surface: Close to 138A; venation, close to 141B.

Flower description:

*Flower type and habit.*—Single cup-shaped flowers arranged in compound umbels; flowers face upright to outwardly; freely flowering habit; about four to twelve flowers per inflorescence; about 30 to 60 flowers develop per plant.

*Natural flowering season.*—Flowering continuous from the late spring until the autumn in The Netherlands.

*Fragrance.*—None detected.

*Flower longevity on the plant.*—About one to three weeks; flowers not persistent.

*Flower longevity as a cut flower.*—About one to two weeks; flowers not persistent.

*Flower buds.*—Length: About 4.4 cm. Diameter: About 1.4 cm. Shape: Ovoid. Color: Close to 71A; towards the apex, close to 143A.

*Umbel height.*—About 9 cm.

*Umbel diameter.*—About 12 cm to 14 cm.

*Flower diameter.*—About 5 cm.

*Flower depth* (*height*).—About 5.7 cm.

*Perianth.*—Arrangement: Six arranged in two whorls, each whorl with two lateral and one median segments. Size, inner perianth: Length, lateral segments: About 6.2 cm. Width, lateral segments: About 1.7 cm. Length, median segment: About 5.1 cm. Width, median segment: About 1.8 cm. Size, outer perianth: Length, lateral segments: About 6.2 cm. Width, lateral segments: About 3.3 cm. Length, median segment: About 5.9 cm. Width, median segment: About 3.3 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner and outer perianths, lateral and median segments: Attenuate. Margin, inner and outer perianths, lateral and median segments: Entire. Texture, inner and outer perianths, lateral and median segments: Smooth glabrous. Color, inner perianth: When opening and fully opened, lateral segments, upper surface: Towards the apex, close to 72A; mid-section, close to 5B; towards the base, close to 68B; stripes, close to N77A. When opening and fully opened, median segment, upper surface: Close to 72D; towards the apex, close to 72A. When opening and fully opened, lateral segments, lower surface: Close to 72A; towards the base, close to 5B. When opening and fully opened, median segment, lower surface: Close to N74D; towards the baser, close to 72B. Color, outer perianth: When opening and fully opened, lateral segments, upper surface: Close to 70A; towards the apex, close to 72B. When opening and fully opened, median segment, upper surface: Close to 72A; towards the apex, close to 71C. When opening and fully opened, lateral segments, lower surface: Close to 70A; towards the apex, close to 71A; venation, close to 143C. When opening and fully opened, median segment, lower surface: Close to 72A; towards the apex, close to 71A; venation, close to 143C.

*Pedicels.*—Length: About 1.4 cm. Diameter: About 3 mm. Strength: Strong. Angle: About 50° from vertical. Texture: Smooth, glabrous. Color: Close to 144A.

*Reproductive organs.*—Stamens: Quantity per flower: Six. Anther shape: Oval. Anther size: About 2 mm by 7 mm. Anther color: Close to 199C. Pollen amount: Abundant. Pollen color: Close to 188B. Pistils: Quantity per flower: One. Pistil length: About 4.4 cm. Style length: About 3.4 cm. Style color: Close to 70B. Stigma color: Close to 72A. Ovary color: Close to 144A.

*Fruits.*—Length: About 1.5 cm. Diameter: About 1.2 cm. Color: Close to 144A.

*Seeds.*—None observed.

Disease/pest resistance: Plants of the new *Alstroemeria* have not been observed to be resistant to pathogens and pests common to *Alstroemeria.*

Garden performance: Plants of the new *Alstroemeria* have been observed to have good garden performance and to tolerate wind, rain and temperatures ranging from about 6° C. to about 30° C.

It is claimed:

1. A new and distinct *Alstroemeria* plant named 'Koncayuko' as illustrated and described.

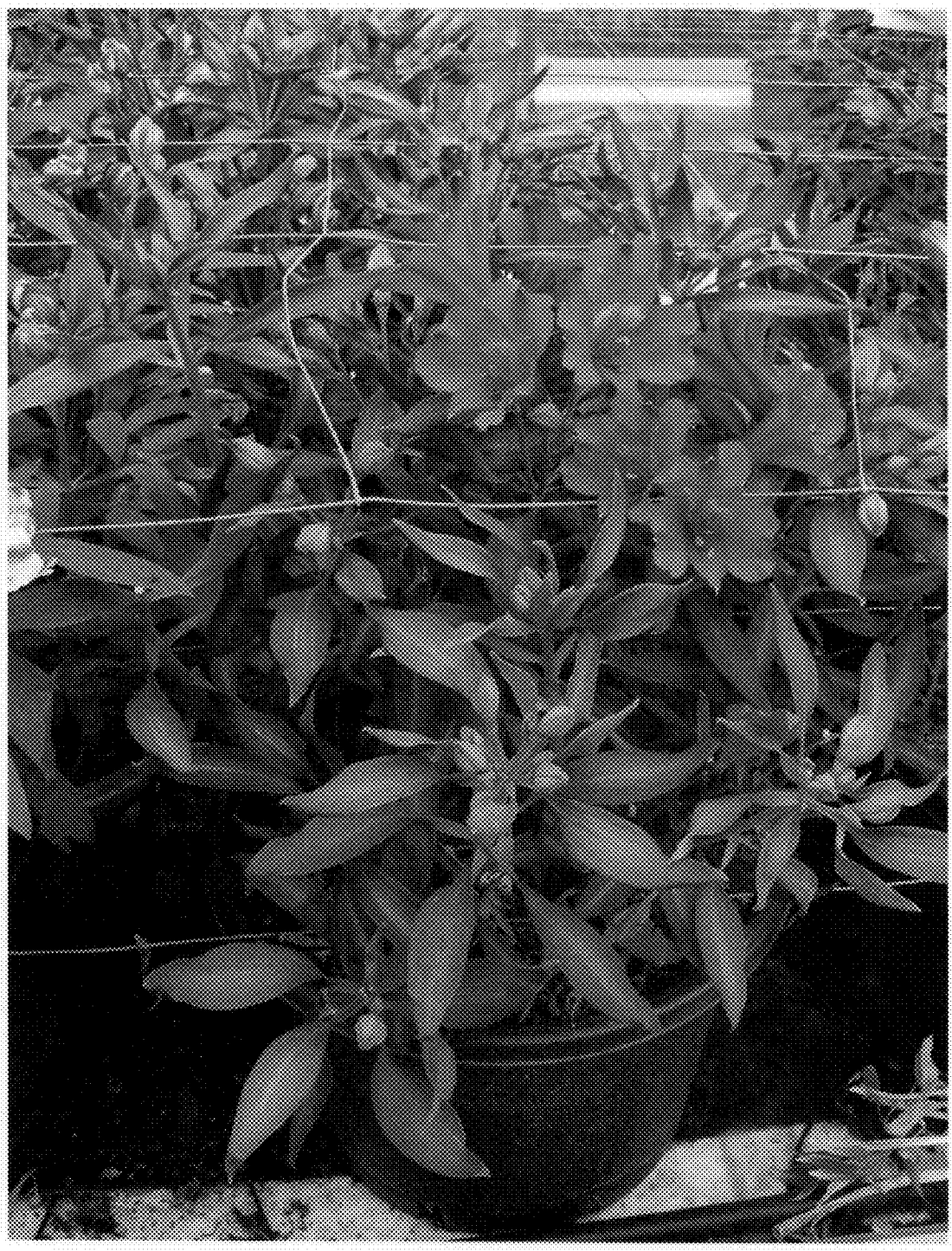

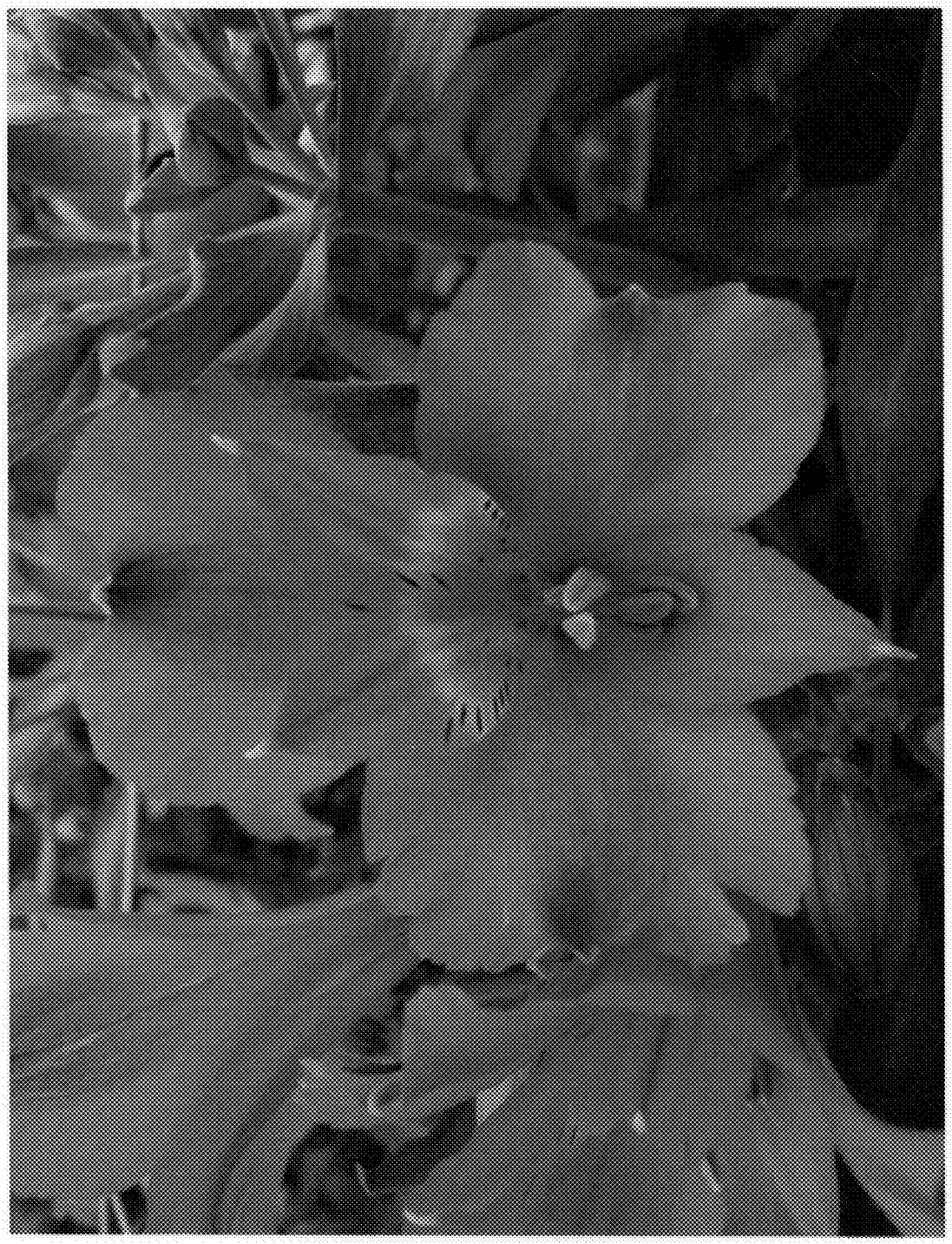

* * * * *